United States Patent
Gliner et al.

(10) Patent No.: US 11,918,341 B2
(45) Date of Patent: Mar. 5, 2024

(54) SELECTIVE GRAPHICAL PRESENTATION OF ELECTROPHYSIOLOGICAL PARAMETERS

(71) Applicant: Biosense Webster (Israel) Ltd., Yokneam (IL)

(72) Inventors: Vadim Gliner, Haifa (IL); Alexander Salevich, Haifa (IL); Yair Palti, Herzelia (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 17/851,199

(22) Filed: Jun. 28, 2022

(65) Prior Publication Data

US 2023/0083715 A1 Mar. 16, 2023

Related U.S. Application Data (63) Continuation of application No. 16/723,592, filed on Dec. 20, 2019, now Pat. No. 11,517,218.

(51) Int. Cl.
*A61B 5/00* (2006.01)
*A61B 5/06* (2006.01)
(Continued)

(52) U.S. Cl.
CPC .............. *A61B 5/062* (2013.01); *A61B 5/287* (2021.01); *A61B 5/339* (2021.01); *A61B 34/20* (2016.02); *G06T 19/003* (2013.01)

(58) Field of Classification Search
CPC .......... A61B 5/062; A61B 5/339; A61B 5/287
See application file for complete search history.

(56) References Cited

U.S. PATENT DOCUMENTS

| 4,699,147 A | 10/1987 | Chilson et al. |
| 4,940,064 A | 7/1990 | Desai |

(Continued)

FOREIGN PATENT DOCUMENTS

| CN | 111248993 A | 6/2020 |
| CN | 111248996 A | 6/2020 |

(Continued)

OTHER PUBLICATIONS

Extended European Search Report issued in Application No. EP 20215542.0; dated May 17, 2021, 8 pages.

*Primary Examiner* — Joel F Brutus
(74) *Attorney, Agent, or Firm* — Troutman Pepper Hamilton Sanders LLP (57) ABSTRACT

A medical apparatus includes a probe configured for insertion into a body of a patient. The probe includes electrodes configured to contact tissue within the body. The apparatus further includes a display screen, a position-tracking system configured to acquire position coordinates of the electrodes, and a processor. The processor is configured to acquire electrophysiological signals from a group of the electrodes in a sequence of time intervals, extract electrophysiological parameters from the signals, and for each time interval, compute a measure of consistency of the parameters extracted from the signals. The processor is further configured to render to the display screen a three-dimensional map of the tissue while superimposing on the map a visual indication of the extracted parameters for which the measure of consistency satisfied a consistency criterion, and automatically discarding from the map the parameters for which the measure of consistency did not satisfy the criterion.

19 Claims, 3 Drawing Sheets

(51) Int. Cl.
  *A61B 5/287* (2021.01)
  *A61B 5/339* (2021.01)
  *A61B 34/20* (2016.01)
  *G06T 19/00* (2011.01)

(56) References Cited

U.S. PATENT DOCUMENTS

| | | |
|---|---|---|
| 5,215,103 A | 6/1993 | Desai |
| 5,255,679 A | 10/1993 | Imran |
| 5,293,869 A | 3/1994 | Edwards et al. |
| 5,309,910 A | 5/1994 | Edwards et al. |
| 5,313,943 A | 5/1994 | Houser et al. |
| 5,324,284 A | 6/1994 | Imran |
| 5,345,936 A | 9/1994 | Pomeranz et al. |
| 5,365,926 A | 11/1994 | Desai |
| 5,391,199 A | 2/1995 | Ben-Haim |
| 5,396,887 A | 3/1995 | Imran |
| 5,400,783 A | 3/1995 | Pomeranz et al. |
| 5,411,025 A | 5/1995 | Webster, Jr. |
| 5,415,166 A | 5/1995 | Imran |
| 5,456,254 A | 10/1995 | Pietroski et al. |
| 5,465,717 A | 11/1995 | Imran et al. |
| 5,476,495 A | 12/1995 | Kordis et al. |
| 5,499,981 A | 3/1996 | Kordis |
| 5,526,810 A | 6/1996 | Wang |
| 5,546,940 A | 8/1996 | Panescu et al. |
| 5,549,108 A | 8/1996 | Edwards et al. |
| 5,558,073 A | 9/1996 | Pomeranz et al. |
| 5,577,509 A | 11/1996 | Panescu et al. |
| 5,595,183 A | 1/1997 | Swanson et al. |
| 5,598,848 A | 2/1997 | Swanson et al. |
| 5,609,157 A | 3/1997 | Panescu et al. |
| 5,628,313 A | 5/1997 | Webster, Jr. |
| 5,681,280 A | 10/1997 | Rusk et al. |
| 5,722,401 A | 3/1998 | Pietroski et al. |
| 5,722,403 A | 3/1998 | McGee et al. |
| 5,725,525 A | 3/1998 | Kordis |
| 5,730,128 A | 3/1998 | Pomeranz et al. |
| 5,772,590 A | 6/1998 | Webster, Jr. |
| 5,782,899 A | 7/1998 | Imran |
| 5,823,189 A | 10/1998 | Kordis |
| 5,881,727 A | 3/1999 | Edwards |
| 5,893,847 A | 4/1999 | Kordis |
| 5,904,680 A | 5/1999 | Kordis et al. |
| 5,911,739 A | 6/1999 | Kordis et al. |
| 5,928,228 A | 7/1999 | Kordis et al. |
| 5,968,040 A | 10/1999 | Swanson et al. |
| 6,014,579 A | 1/2000 | Pomeranz et al. |
| 6,014,590 A | 1/2000 | Whayne et al. |
| 6,119,030 A | 9/2000 | Morency |
| 6,216,043 B1 | 4/2001 | Swanson et al. |
| 6,216,044 B1 | 4/2001 | Kordis |
| 6,236,883 B1 | 5/2001 | Ciaccio et al. |
| 6,239,724 B1 | 5/2001 | Doron et al. |
| 6,332,089 B1 | 12/2001 | Acker et al. |
| 6,428,537 B1 | 8/2002 | Swanson et al. |
| 6,456,864 B1 | 9/2002 | Swanson et al. |
| 6,484,118 B1 | 11/2002 | Govari et al. |
| 6,574,492 B1 | 6/2003 | Ben-Haim et al. |
| 6,584,345 B2 | 6/2003 | Govari |
| 6,600,948 B2 | 7/2003 | Ben-Haim et al. |
| 6,618,612 B1 | 9/2003 | Acker et al. |
| 6,690,963 B2 | 2/2004 | Ben-Haim et al. |
| 6,738,655 B1 | 5/2004 | Sen et al. |
| 6,741,878 B2 | 5/2004 | Fuimaono et al. |
| 6,748,255 B2 | 6/2004 | Fuimaono et al. |
| 6,780,183 B2 | 8/2004 | Jimenez, Jr. et al. |
| 6,837,886 B2 | 1/2005 | Collins et al. |
| 6,866,662 B2 | 3/2005 | Fuimaono et al. |
| 6,892,091 B1 | 5/2005 | Ben-Haim et al. |
| 6,970,730 B2 | 11/2005 | Fuimaono et al. |
| 6,973,340 B2 | 12/2005 | Fuimaono et al. |
| 6,980,858 B2 | 12/2005 | Fuimaono et al. |
| 7,048,734 B1 | 5/2006 | Fleischman et al. |
| 7,149,563 B2 | 12/2006 | Fuimaono et al. |
| 7,255,695 B2 | 8/2007 | Falwell et al. |
| 7,257,434 B2 | 8/2007 | Fuimaono et al. |
| 7,399,299 B2 | 7/2008 | Daniel et al. |
| 7,410,486 B2 | 8/2008 | Fuimaono et al. |
| 7,522,950 B2 | 4/2009 | Fuimaono et al. |
| RE41,334 E | 5/2010 | Beatty et al. |
| 7,846,157 B2 | 12/2010 | Kozel |
| 7,930,018 B2 | 4/2011 | Harlev et al. |
| 8,007,495 B2 | 8/2011 | McDaniel et al. |
| 8,048,063 B2 | 11/2011 | Aeby et al. |
| 8,103,327 B2 | 1/2012 | Harlev et al. |
| 8,167,845 B2 | 5/2012 | Wang et al. |
| 8,224,416 B2 | 7/2012 | De La Rama et al. |
| 8,235,988 B2 | 8/2012 | Davis et al. |
| 8,346,339 B2 | 1/2013 | Kordis et al. |
| 8,435,232 B2 | 5/2013 | Aeby et al. |
| 8,447,377 B2 | 5/2013 | Harlev et al. |
| 8,498,686 B2 | 7/2013 | Grunewald |
| 8,517,999 B2 | 8/2013 | Pappone et al. |
| 8,545,490 B2 | 10/2013 | Mihajlovic et al. |
| 8,560,086 B2 | 10/2013 | Just et al. |
| 8,567,265 B2 | 10/2013 | Aeby et al. |
| 8,712,550 B2 | 4/2014 | Grunewald |
| 8,755,861 B2 | 6/2014 | Harlev et al. |
| 8,825,130 B2 | 9/2014 | Just et al. |
| 8,906,011 B2 | 12/2014 | Gelbart et al. |
| 8,945,120 B2 | 2/2015 | McDaniel et al. |
| 8,979,839 B2 | 3/2015 | De La Rama et al. |
| 9,037,264 B2 | 5/2015 | Just et al. |
| 9,131,980 B2 | 9/2015 | Bloom |
| 9,204,929 B2 | 12/2015 | Solis |
| 9,277,960 B2 | 3/2016 | Weinkam et al. |
| 9,314,208 B1 | 4/2016 | Altmann et al. |
| 9,339,331 B2 | 5/2016 | Tegg et al. |
| 9,486,282 B2 | 11/2016 | Solis |
| 9,554,718 B2 | 1/2017 | Bar-Tal et al. |
| D782,686 S | 3/2017 | Werneth et al. |
| 9,585,588 B2 | 3/2017 | Marecki et al. |
| 9,597,036 B2 | 3/2017 | Aeby et al. |
| 9,687,297 B2 | 6/2017 | Just et al. |
| 9,693,733 B2 | 7/2017 | Altmann et al. |
| 9,782,099 B2 | 10/2017 | Williams et al. |
| 9,788,895 B2 | 10/2017 | Solis |
| 9,801,681 B2 | 10/2017 | Laske et al. |
| 9,814,618 B2 | 11/2017 | Nguyen et al. |
| 9,833,161 B2 | 12/2017 | Govari |
| 9,894,756 B2 | 2/2018 | Weinkam et al. |
| 9,895,073 B2 | 2/2018 | Solis |
| 9,907,609 B2 | 3/2018 | Cao et al. |
| 9,974,460 B2 | 5/2018 | Wu et al. |
| 9,986,949 B2 | 6/2018 | Govari et al. |
| 9,993,160 B2 | 6/2018 | Salvestro et al. |
| 10,014,607 B1 | 7/2018 | Govari et al. |
| 10,028,376 B2 | 7/2018 | Weinkam et al. |
| 10,034,637 B2 | 7/2018 | Harlev et al. |
| 10,039,494 B2 | 8/2018 | Altmann et al. |
| 10,045,707 B2 | 8/2018 | Govari |
| 10,078,713 B2 | 9/2018 | Auerbach et al. |
| 10,111,623 B2 | 10/2018 | Jung et al. |
| 10,130,420 B2 | 11/2018 | Basu et al. |
| 10,136,828 B2 | 11/2018 | Houben et al. |
| 10,143,394 B2 | 12/2018 | Solis |
| 10,172,536 B2 | 1/2019 | Maskara et al. |
| 10,182,762 B2 | 1/2019 | Just et al. |
| 10,194,818 B2 | 2/2019 | Williams et al. |
| 10,201,311 B2 | 2/2019 | Chou et al. |
| 10,219,860 B2 | 3/2019 | Harlev et al. |
| 10,219,861 B2 | 3/2019 | Just et al. |
| 10,231,328 B2 | 3/2019 | Weinkam et al. |
| 10,238,309 B2 | 3/2019 | Bar-Tal et al. |
| 10,278,590 B2 | 5/2019 | Salvestro et al. |
| D851,774 S | 6/2019 | Werneth et al. |
| 10,314,505 B2 | 6/2019 | Williams et al. |
| 10,314,507 B2 | 6/2019 | Govari et al. |
| 10,314,648 B2 | 6/2019 | Ge et al. |
| 10,314,649 B2 | 6/2019 | Bakos et al. |
| 10,349,855 B2 | 7/2019 | Zeidan et al. |
| 10,350,003 B2 | 7/2019 | Weinkam et al. |
| 10,362,991 B2 | 7/2019 | Tran et al. |

(56) References Cited

U.S. PATENT DOCUMENTS

| | | | |
|---|---|---|---|
| 10,375,827 B2 | 8/2019 | Weinkam et al. |
| 10,376,170 B2 | 8/2019 | Quinn et al. |
| 10,376,221 B2 | 8/2019 | Iyun et al. |
| 10,398,348 B2 | 9/2019 | Osadchy et al. |
| 10,403,053 B2 | 9/2019 | Katz et al. |
| 10,441,188 B2 | 10/2019 | Katz et al. |
| 10,470,682 B2 | 11/2019 | Deno et al. |
| 10,470,714 B2 | 11/2019 | Altmann et al. |
| 10,482,198 B2 | 11/2019 | Auerbach et al. |
| 10,492,857 B2 | 12/2019 | Guggenberger et al. |
| 10,542,620 B2 | 1/2020 | Weinkam et al. |
| 10,575,743 B2 | 3/2020 | Basu et al. |
| 10,575,745 B2 | 3/2020 | Solis |
| 10,582,871 B2 | 3/2020 | Williams et al. |
| 10,582,894 B2 | 3/2020 | Ben Zrihem et al. |
| 10,596,346 B2 | 3/2020 | Aeby et al. |
| 10,602,947 B2 | 3/2020 | Govari et al. |
| 10,617,867 B2 | 4/2020 | Viswanathan et al. |
| 10,660,702 B2 | 5/2020 | Viswanathan et al. |
| 10,667,753 B2 | 6/2020 | Werneth et al. |
| 10,674,929 B2 | 6/2020 | Houben et al. |
| 10,681,805 B2 | 6/2020 | Weinkam et al. |
| 10,682,181 B2 | 6/2020 | Cohen et al. |
| 10,687,892 B2 | 6/2020 | Long et al. |
| 10,702,178 B2 | 7/2020 | Dahlen et al. |
| 10,716,477 B2 | 7/2020 | Salvestro et al. |
| 10,758,304 B2 | 9/2020 | Aujla |
| 10,765,371 B2 | 9/2020 | Hayam et al. |
| 10,772,566 B2 | 9/2020 | Aujila |
| 10,799,281 B2 | 10/2020 | Goertzen et al. |
| 10,842,558 B2 | 11/2020 | Harlev et al. |
| 10,842,561 B2 | 11/2020 | Viswanathan et al. |
| 10,863,914 B2 | 12/2020 | Govari et al. |
| 10,881,376 B2 | 1/2021 | Shemesh et al. |
| 10,898,139 B2 | 1/2021 | Guta et al. |
| 10,905,329 B2 | 2/2021 | Bar-Tal et al. |
| 10,912,484 B2 | 2/2021 | Ziv-Ari et al. |
| 10,918,306 B2 | 2/2021 | Govari et al. |
| 10,939,871 B2 | 3/2021 | Altmann et al. |
| 10,952,795 B2 | 3/2021 | Cohen et al. |
| 10,973,426 B2 | 4/2021 | Williams et al. |
| 10,973,461 B2 | 4/2021 | Baram et al. |
| 10,987,045 B2 | 4/2021 | Basu et al. |
| 11,006,902 B1 | 5/2021 | Bonyak et al. |
| 11,040,208 B1 | 6/2021 | Govari et al. |
| 11,045,628 B2 | 6/2021 | Beeckler et al. |
| 11,051,877 B2 | 7/2021 | Sliwa et al. |
| 11,109,788 B2 | 9/2021 | Rottmann et al. |
| 11,116,435 B2 | 9/2021 | Urman et al. |
| 11,129,574 B2 | 9/2021 | Cohen et al. |
| 11,160,482 B2 | 11/2021 | Solis |
| 11,164,371 B2 | 11/2021 | Yellin et al. |
| 2002/0065455 A1 | 5/2002 | Ben-Haim et al. |
| 2003/0120150 A1 | 6/2003 | Govari |
| 2004/0068178 A1 | 4/2004 | Govari |
| 2004/0210121 A1 | 10/2004 | Fuimaono et al. |
| 2006/0009689 A1 | 1/2006 | Fuimaono et al. |
| 2006/0009690 A1 | 1/2006 | Fuimaono et al. |
| 2006/0100669 A1 | 5/2006 | Fuimaono et al. |
| 2007/0093806 A1 | 4/2007 | Desai et al. |
| 2007/0276212 A1 | 11/2007 | Fuimaono et al. |
| 2008/0234564 A1 | 9/2008 | Beatty et al. |
| 2011/0118726 A1 | 5/2011 | De La Rama et al. |
| 2011/0160574 A1 | 6/2011 | Harlev et al. |
| 2011/0190625 A1 | 8/2011 | Harlev et al. |
| 2011/0245756 A1 | 10/2011 | Arora et al. |
| 2011/0301597 A1 | 12/2011 | McDaniel et al. |
| 2012/0101398 A1 | 4/2012 | Ramanathan et al. |
| 2013/0006131 A1 | 1/2013 | Narayan et al. |
| 2013/0172872 A1 | 7/2013 | Subramaniam et al. |
| 2013/0172883 A1 | 7/2013 | Lopes et al. |
| 2013/0178850 A1 | 7/2013 | Lopes et al. |
| 2013/0190587 A1 | 7/2013 | Lopes et al. |
| 2013/0296852 A1 | 11/2013 | Madjarov et al. |
| 2014/0025069 A1 | 1/2014 | Willard et al. |
| 2014/0052118 A1 | 2/2014 | Laske et al. |
| 2014/0180147 A1 | 6/2014 | Thakur et al. |
| 2014/0180151 A1 | 6/2014 | Maskara et al. |
| 2014/0180152 A1 | 6/2014 | Maskara et al. |
| 2014/0257069 A1 | 9/2014 | Eliason et al. |
| 2014/0276712 A1 | 9/2014 | Mallin et al. |
| 2014/0309512 A1 | 10/2014 | Govari et al. |
| 2015/0011991 A1 | 1/2015 | Buysman et al. |
| 2015/0045863 A1 | 2/2015 | Litscher et al. |
| 2015/0057507 A1 | 2/2015 | Koyrakh et al. |
| 2015/0080693 A1 | 3/2015 | Solis |
| 2015/0105770 A1 | 4/2015 | Amit |
| 2015/0119878 A1 | 4/2015 | Heisel et al. |
| 2015/0133919 A1 | 5/2015 | McDaniel et al. |
| 2015/0208942 A1 | 7/2015 | Bar-Tal et al. |
| 2015/0250424 A1 | 9/2015 | Govari et al. |
| 2015/0270634 A1 | 9/2015 | Buesseler et al. |
| 2015/0342532 A1 | 12/2015 | Basu et al. |
| 2016/0045123 A1* | 2/2016 | Bar-Tal .............. A61B 5/287 |
| | | 600/515 |
| 2016/0081746 A1 | 3/2016 | Solis |
| 2016/0100770 A1 | 4/2016 | Afonso et al. |
| 2016/0113582 A1 | 4/2016 | Altmann et al. |
| 2016/0113709 A1 | 4/2016 | Maor |
| 2016/0183877 A1 | 6/2016 | Williams et al. |
| 2016/0228023 A1 | 8/2016 | Govari |
| 2016/0228062 A1 | 8/2016 | Altmann et al. |
| 2016/0278853 A1 | 9/2016 | Ogle et al. |
| 2016/0302858 A1 | 10/2016 | Bencini |
| 2016/0338770 A1 | 11/2016 | Bar-Tal et al. |
| 2017/0027638 A1 | 2/2017 | Solis |
| 2017/0065227 A1 | 3/2017 | Marrs et al. |
| 2017/0071543 A1 | 3/2017 | Basu et al. |
| 2017/0071544 A1 | 3/2017 | Basu et al. |
| 2017/0071665 A1 | 3/2017 | Solis |
| 2017/0095173 A1 | 4/2017 | Bar-Tal et al. |
| 2017/0100187 A1 | 4/2017 | Basu et al. |
| 2017/0143227 A1 | 5/2017 | Marecki et al. |
| 2017/0156790 A1 | 6/2017 | Aujla |
| 2017/0172442 A1 | 6/2017 | Govari |
| 2017/0185702 A1 | 6/2017 | Auerbach et al. |
| 2017/0202515 A1 | 7/2017 | Zrihem et al. |
| 2017/0221262 A1 | 8/2017 | Laughner et al. |
| 2017/0224958 A1 | 8/2017 | Cummings et al. |
| 2017/0265812 A1 | 9/2017 | Williams et al. |
| 2017/0281031 A1 | 10/2017 | Houben et al. |
| 2017/0281268 A1 | 10/2017 | Tran et al. |
| 2017/0296125 A1 | 10/2017 | Altmann et al. |
| 2017/0296251 A1 | 10/2017 | Wu et al. |
| 2017/0347959 A1 | 12/2017 | Guta et al. |
| 2017/0354338 A1 | 12/2017 | Levin et al. |
| 2017/0354339 A1 | 12/2017 | Zeidan et al. |
| 2017/0354364 A1 | 12/2017 | Bar-Tal et al. |
| 2018/0008203 A1 | 1/2018 | Iyun et al. |
| 2018/0028084 A1 | 2/2018 | Williams et al. |
| 2018/0042505 A1* | 2/2018 | Botzer .............. A61B 5/6869 |
| 2018/0049803 A1 | 2/2018 | Solis |
| 2018/0085064 A1 | 3/2018 | Auerbach et al. |
| 2018/0132749 A1 | 5/2018 | Govari et al. |
| 2018/0137687 A1 | 5/2018 | Katz et al. |
| 2018/0160936 A1 | 6/2018 | Govari et al. |
| 2018/0160978 A1 | 6/2018 | Cohen et al. |
| 2018/0168511 A1 | 6/2018 | Hall et al. |
| 2018/0184982 A1 | 7/2018 | Basu et al. |
| 2018/0192958 A1 | 7/2018 | Wu |
| 2018/0206792 A1 | 7/2018 | Auerbach et al. |
| 2018/0235692 A1 | 8/2018 | Efimov et al. |
| 2018/0249959 A1 | 9/2018 | Osypka |
| 2018/0256109 A1 | 9/2018 | Wu et al. |
| 2018/0279954 A1 | 10/2018 | Hayam et al. |
| 2018/0303414 A1 | 10/2018 | Toth et al. |
| 2018/0310987 A1 | 11/2018 | Altmann et al. |
| 2018/0311497 A1 | 11/2018 | Viswanathan et al. |
| 2018/0338722 A1 | 11/2018 | Altmann et al. |
| 2018/0344188 A1 | 12/2018 | Govari |
| 2018/0344202 A1 | 12/2018 | Bar-Tal et al. |
| 2018/0344251 A1 | 12/2018 | Harlev et al. |
| 2018/0344393 A1 | 12/2018 | Gruba et al. |
| 2018/0360534 A1 | 12/2018 | Teplitsky et al. |

(56) References Cited

U.S. PATENT DOCUMENTS

| | | |
|---|---|---|
| 2018/0365355 A1 | 12/2018 | Auerbach et al. |
| 2019/0000540 A1 | 1/2019 | Cohen et al. |
| 2019/0008582 A1 | 1/2019 | Govari et al. |
| 2019/0015007 A1 | 1/2019 | Rottmann et al. |
| 2019/0030328 A1 | 1/2019 | Stewart et al. |
| 2019/0053708 A1 | 2/2019 | Gliner |
| 2019/0059766 A1 | 2/2019 | Houben et al. |
| 2019/0069950 A1 | 3/2019 | Viswanathan et al. |
| 2019/0069954 A1 | 3/2019 | Cohen et al. |
| 2019/0117111 A1 | 4/2019 | Osadchy et al. |
| 2019/0117303 A1 | 4/2019 | Claude et al. |
| 2019/0117315 A1 | 4/2019 | Keyes et al. |
| 2019/0125439 A1 | 5/2019 | Rohl et al. |
| 2019/0133552 A1 | 5/2019 | Shemesh et al. |
| 2019/0142293 A1 | 5/2019 | Solis |
| 2019/0164633 A1 | 5/2019 | Ingel et al. |
| 2019/0167137 A1 | 6/2019 | Bar-Tal et al. |
| 2019/0167140 A1 | 6/2019 | Williams et al. |
| 2019/0188909 A1 | 6/2019 | Yellin et al. |
| 2019/0201664 A1 | 7/2019 | Govari |
| 2019/0209089 A1 | 7/2019 | Baram et al. |
| 2019/0216346 A1 | 7/2019 | Ghodrati et al. |
| 2019/0216347 A1 | 7/2019 | Ghodrati et al. |
| 2019/0231421 A1 | 8/2019 | Viswanathan et al. |
| 2019/0231423 A1 | 8/2019 | Weinkam et al. |
| 2019/0239811 A1 | 8/2019 | Just et al. |
| 2019/0246935 A1 | 8/2019 | Govari et al. |
| 2019/0298442 A1 | 10/2019 | Ogata et al. |
| 2019/0314083 A1 | 10/2019 | Herrera et al. |
| 2019/0328260 A1 | 10/2019 | Zeidan et al. |
| 2019/0343580 A1 | 11/2019 | Nguyen et al. |
| 2020/0000518 A1 | 1/2020 | Kiernan et al. |
| 2020/0008705 A1 | 1/2020 | Ziv-Ari et al. |
| 2020/0008869 A1 | 1/2020 | Byrd |
| 2020/0009378 A1 | 1/2020 | Stewart et al. |
| 2020/0015890 A1 | 1/2020 | To et al. |
| 2020/0022653 A1 | 1/2020 | Moisa |
| 2020/0029845 A1 | 1/2020 | Baram et al. |
| 2020/0046421 A1 | 2/2020 | Govari |
| 2020/0046423 A1 | 2/2020 | Viswanathan et al. |
| 2020/0060569 A1 | 2/2020 | Tegg |
| 2020/0077959 A1 | 3/2020 | Altmann et al. |
| 2020/0093539 A1 | 3/2020 | Long et al. |
| 2020/0129089 A1 | 4/2020 | Gliner et al. |
| 2020/0129125 A1 | 4/2020 | Govari et al. |
| 2020/0129128 A1 | 4/2020 | Gliner et al. |
| 2020/0179650 A1 | 6/2020 | Beeckler et al. |
| 2020/0196896 A1 | 6/2020 | Solis |
| 2020/0205689 A1 | 7/2020 | Squires et al. |
| 2020/0205690 A1 | 7/2020 | Williams et al. |
| 2020/0205737 A1 | 7/2020 | Beeckler |
| 2020/0205876 A1 | 7/2020 | Govari |
| 2020/0205892 A1 | 7/2020 | Viswanathan et al. |
| 2020/0206461 A1 | 7/2020 | Govari et al. |
| 2020/0206498 A1 | 7/2020 | Arora et al. |
| 2020/0289197 A1 | 9/2020 | Viswanathan et al. |
| 2020/0297234 A1 | 9/2020 | Houben et al. |
| 2020/0297281 A1 | 9/2020 | Basu et al. |
| 2020/0305726 A1 | 10/2020 | Salvestro et al. |
| 2020/0305946 A1 | 10/2020 | DeSimone et al. |
| 2020/0397328 A1 | 12/2020 | Altmann et al. |
| 2020/0398048 A1 | 12/2020 | Krimsky et al. |
| 2021/0015549 A1 | 1/2021 | Haghighi-Mood et al. |
| 2021/0022684 A1 | 1/2021 | Govari et al. |
| 2021/0045805 A1 | 2/2021 | Govari et al. |
| 2021/0059549 A1 | 3/2021 | Urman et al. |
| 2021/0059550 A1 | 3/2021 | Urman et al. |
| 2021/0059608 A1 | 3/2021 | Beeckler et al. |
| 2021/0059743 A1 | 3/2021 | Govari |
| 2021/0059747 A1 | 3/2021 | Krans et al. |
| 2021/0077184 A1 | 3/2021 | Basu et al. |
| 2021/0082157 A1 | 3/2021 | Rosenberg et al. |
| 2021/0085200 A1 | 3/2021 | Auerbach et al. |
| 2021/0085204 A1 | 3/2021 | Auerbach et al. |
| 2021/0085215 A1 | 3/2021 | Auerbach et al. |
| 2021/0085387 A1 | 3/2021 | Amit et al. |
| 2021/0093292 A1 | 4/2021 | Baram et al. |
| 2021/0093294 A1 | 4/2021 | Shemesh et al. |
| 2021/0093374 A1 | 4/2021 | Govari et al. |
| 2021/0093377 A1 | 4/2021 | Herrera et al. |
| 2021/0100612 A1 | 4/2021 | Baron et al. |
| 2021/0113822 A1 | 4/2021 | Beeckler et al. |
| 2021/0127999 A1 | 5/2021 | Govari et al. |
| 2021/0128010 A1 | 5/2021 | Govari et al. |
| 2021/0133516 A1 | 5/2021 | Govari et al. |
| 2021/0145282 A1 | 5/2021 | Bar-Tal et al. |
| 2021/0169421 A1 | 6/2021 | Govari |
| 2021/0169568 A1 | 6/2021 | Govari et al. |
| 2021/0177294 A1 | 6/2021 | Gliner et al. |
| 2021/0177356 A1 | 6/2021 | Gliner et al. |
| 2021/0178166 A1 | 6/2021 | Govari et al. |
| 2021/0186363 A1 | 6/2021 | Gliner et al. |
| 2021/0187241 A1 | 6/2021 | Govari et al. |
| 2021/0196372 A1 | 7/2021 | Altmann et al. |
| 2021/0196394 A1 | 7/2021 | Govari et al. |
| 2021/0212591 A1 | 7/2021 | Govari et al. |
| 2021/0219904 A1 | 7/2021 | Yarnitsky et al. |
| 2021/0278936 A1 | 9/2021 | Katz et al. |
| 2021/0282659 A1 | 9/2021 | Govari et al. |
| 2021/0307815 A1 | 10/2021 | Govari et al. |
| 2021/0308424 A1 | 10/2021 | Beeckler et al. |
| 2021/0338319 A1 | 11/2021 | Govari et al. |

FOREIGN PATENT DOCUMENTS

| | | |
|---|---|---|
| EP | 0668740 A1 | 8/1995 |
| EP | 0644738 B1 | 3/2000 |
| EP | 0727183 B1 | 11/2002 |
| EP | 0727184 B1 | 12/2002 |
| EP | 2783651 A1 | 10/2014 |
| EP | 2699151 B1 | 11/2015 |
| EP | 2699152 B1 | 11/2015 |
| EP | 2699153 B1 | 12/2015 |
| EP | 2498706 B1 | 4/2016 |
| EP | 2578173 B1 | 6/2017 |
| EP | 3238645 A1 | 11/2017 |
| EP | 2884931 B1 | 1/2018 |
| EP | 2349440 B1 | 8/2019 |
| EP | 3318211 B1 | 12/2019 |
| EP | 3581135 A1 | 12/2019 |
| EP | 2736434 B1 | 2/2020 |
| EP | 3451962 B1 | 3/2020 |
| EP | 3972510 A1 | 3/2022 |
| WO | 9421167 A1 | 9/1994 |
| WO | 9421169 A1 | 9/1994 |
| WO | 9605768 A1 | 2/1996 |
| WO | 9625095 A1 | 8/1996 |
| WO | 9634560 A1 | 11/1996 |
| WO | 0182814 B1 | 5/2002 |
| WO | 2004087249 A2 | 10/2004 |
| WO | 2012100185 A2 | 7/2012 |
| WO | 2013052852 A1 | 4/2013 |
| WO | 2013162884 A1 | 10/2013 |
| WO | 2013173917 A1 | 11/2013 |
| WO | 2013176881 A1 | 11/2013 |
| WO | 2014176205 A1 | 10/2014 |
| WO | 2016019760 A1 | 2/2016 |
| WO | 2016044687 A1 | 3/2016 |
| WO | 2018111600 A1 | 6/2018 |
| WO | 2018191149 A1 | 10/2018 |
| WO | 2019084442 A1 | 5/2019 |
| WO | 2019143960 A1 | 7/2019 |
| WO | 2020026217 A1 | 2/2020 |
| WO | 2020185339 A1 | 9/2020 |
| WO | 2020206328 A1 | 10/2020 |

\* cited by examiner

SELECTIVE GRAPHICAL PRESENTATION OF ELECTROPHYSIOLOGICAL PARAMETERS

CROSS-REFERENCE TO RELATED APPLICATIONS

This application is a continuation application of U.S. patent application Ser. No. 16/723,592 filed 20 Dec. 2019, the entire contents of which is incorporated herein by reference.

FIELD OF THE INVENTION

The present invention relates generally to electrophysiological measurements, and particularly to apparatus and methods for automated mapping of electrophysiological parameters.

BACKGROUND

An electrophysiological (EP) map of a tissue of a patient is generated by positioning one or more electrodes on a region of the tissue, acquiring an EP signal of the region, and then repeating the process for a different region. EP parameters are extracted from the EP signals in each region of measurement, and then displayed over an image of the tissue.

SUMMARY

Embodiments of the present invention that are described hereinbelow provide improved methods and apparatus for mapping of electrophysiological parameters.

There is therefore provided, in accordance with an embodiment of the present invention, a medical apparatus, which includes a probe configured for insertion into a body of a patient. The probe includes a plurality of electrodes configured to contact tissue within the body in a sequence of time intervals. The apparatus further includes a display screen, a position-tracking system configured to acquire position coordinates of the electrodes within the body, and a processor.

The processor is configured to acquire respective electrophysiological signals from a group of the electrodes in each time interval in the sequence while the electrodes contact an area of the tissue at respective locations within the area, to extract respective electrophysiological parameters from the respective electrophysiological signals acquired in each time interval by the electrodes in the group, and, for each time interval, to compute a respective measure of consistency among the respective electrophysiological parameters extracted from the electrophysiological signals acquired by the electrodes in the group during the time interval. The processor is further configured to render to the display screen a three-dimensional (3D) map of the tissue while superimposing on the map, responsively to the position coordinates, a visual indication of the extracted electrophysiological parameters at the respective locations of the electrodes in the time intervals for which the respective measure of consistency satisfied a predefined consistency criterion, and to discard automatically from the map the electrophysiological parameters extracted in the time intervals for which the respective measure of consistency did not satisfy the predefined consistency criterion.

In some embodiments, the electrophysiological parameter includes a local activation time (LAT) in a heart of the patient, and the measure of consistency is indicative of a variation of the LAT. In one embodiment, the measure of consistency includes a peak-to-peak variation of the LAT in any given time interval, and the consistency criterion requires that the peak-to-peak variation of the LAT not exceed a predefined limit.

Alternatively or additionally, the electrophysiological parameter includes an electrophysiological voltage, and the measure of consistency is indicative of a variation of the electrophysiological voltage. In one embodiment, the measure of consistency includes a peak-to-peak variation of the electrophysiological voltage in any given time interval, and the consistency criterion requires that the peak-to-peak variation of the electrophysiological voltage not exceed a predefined limit.

In yet another embodiment, the 3D map is rendered in a background color, and the visual indication includes other colors superimposed on the background color at the respective locations to indicate a value of the extracted electrophysiological parameter.

There is also provided, in accordance with an embodiment of the present invention, a method for electrophysiological mapping. The method includes acquiring in a sequence of time intervals respective electrophysiological signals from a group of electrodes on a probe while the electrodes contact an area of tissue within a body of a patient, and acquiring position coordinates of the group of electrodes. Respective electrophysiological parameters are extracted from the respective electrophysiological signals acquired in each time interval in the sequence by the electrodes in the group, and a respective measure of consistency is computed for each time interval among the respective electrophysiological parameters extracted from the electrophysiological signals acquired by the electrodes in the group during the time interval. The method further includes displaying a three-dimensional (3D) map of the tissue while superimposing on the map, responsively to the position coordinates, a visual indication of the extracted electrophysiological parameters at the respective locations in the time intervals for which the respective measure of consistency satisfied a predefined consistency criterion, and automatically discarding from the map the electrophysiological parameters extracted in the time intervals for which the respective measure of consistency did not satisfy the predefined consistency criterion.

The present invention will be more fully understood from the following detailed description of the embodiments thereof, taken together with the drawings in which:

DETAILED DESCRIPTION OF EMBODIMENTS

Overview

Generating an electrophysiological (EP) map of a tissue of a patient involves positioning one or more electrodes on a region of the tissue, acquiring the signal of the region, and then repeating the process for a different region. When small numbers of electrodes are used, this process generates accurate maps of the EP parameters extracted from these signals, since the physician can observe the acquired signals, and only accept "good" signals (as judged by the physician) into the map. A good signal is typically generated only when the electrode is in good contact with the tissue. Using a small number of electrodes has, however, the drawback that the mapping takes a long time.

For catheters with large numbers of electrodes, the mapping time is reduced, but the accuracy is decreased, since the physician is incapable of properly inspecting all the simultaneously generated signals within the available time. The task of accepting good signals (and rejecting others) may be facilitated by presenting to the physician the analyzed results of the signals, i.e., the values of an EP parameter across the measured region. (For the sake of brevity, "value of an EP parameter" will in the following description be referred to simply as "EP parameter.") The task may be further facilitated by presenting these values in a graphical form, such as a map of the values. However, the physician is still required to use his/her subjective judgement in accepting or rejecting the analyzed results, with an inherent variability in the acceptance due to subjectivity. Moreover, requiring the physician to judge the quality of these results will further tax his/her time and attention during the mapping procedure, especially if a large number of electrodes is used.

The embodiments of the present invention that are described herein address these problems by providing a medical apparatus comprising a probe, a display screen, a position-tracking system, and a processor. The probe, which comprises multiple electrodes, is inserted into the body of a patient so that a group of the electrodes contacts an area of tissue within the body. The group of electrodes can include all the electrodes on the probe or a certain subset of the electrodes. (For example, the group may include 20 electrodes that contact a certain area of myocardial tissue, typically an area on the order of 1-10 $cm^2$, out of a total of 120 electrodes on a basket catheter.) While the electrodes contact the tissue, the processor acquires EP signals from the electrodes in a sequence of time intervals, such as a sequence of heartbeats. Simultaneously, the position-tracking system acquires the position coordinates of the electrodes.

For each time interval, the processor extracts the respective EP parameters from the signals, and computes a measure of consistency of the values of the EP parameters across the electrodes in the group. For brevity, the EP parameters extracted at a given time interval from the group of electrodes contacting an area of the tissue will be referred to as a "set of EP parameters." The processor renders to the display screen a three-dimensional (3D) map of the tissue while superimposing on the map a visual indication, such as colors representing the parameter values, of the set of EP parameters for the points in time for which the measure of consistency satisfied a predefined consistency criterion. The processor automatically discards from the map the EP parameters for which the respective measure of consistency did not satisfy the predefined criterion.

This approach facilitates an automatic presentation of a map of valid EP parameters, without having to rely on a subjective and time-consuming assessment of the EP signals or parameters by the physician.

In a disclosed embodiment, the processor displays a 3D map of a chamber of the heart in which EP parameter is being mapped. The 3D map is presented in a neutral tone, such as gray. The EP parameter may comprise, for example, a local activation time (LAT) measured in the myocardium or a bipolar or unipolar maximum voltage. LAT is the time interval between a reference time determined, for example, from the body surface ECG or intracardiac electrogram, and the time of the local depolarization event. Other useful scalar functions of the physiological parameters may be calculated and displayed, superimposed on a combined display of LAT (as pseudocolor) and/or propagation velocity (as arrows). One such useful scalar function is the range of voltages measured at each sampled point (displayed as a pseudo-color): An abnormally low range is diagnostic of scar tissue, upon which the conduction velocity may be displayed as arrows. LAT can be determined manually or automatically, for example, by marking one or more of (a) the maximum negative slope of the voltage of the unipolar recording (−dV/dt); (b) the maximum absolute voltage of the bipolar recording; (c) the maximum absolute slope dV/dt of the bipolar recording; or (d) the minimum voltage of the bipolar recording. (Methods for automated computation of the LAT are known in the art, for example as implemented in the CARTO® system, produced by Biosense Webster Inc., Irvine, Calif.)

During the measurement process in the heart, the processor extracts a set of EP parameters in each of several (for example 3-7) heartbeats from all of the electrodes contacting the tissue. (Alternatively, time intervals for the measurements may be independent of the heartbeats.) As the area where the electrodes contact the tissue is small by comparison with the chamber of the heart, the EP parameters within a set are expected to vary from each other by only a small amount. Therefore, a large variability between the EP parameters of a set is an indication of improper acquisition of the EP signals. A reason for improper EP signal acquisition may be, for example, poor contact between one or more electrodes and the tissue. In order to identify and reject improperly-acquired EP signals, the processor computes a measure of consistency within each set of EP parameters. The measure of consistency may be, for example, a peak-to-peak variation within the set of EP parameters across the group of electrodes.

The processor rejects sets of EP parameters for which the measure of consistency does not satisfy a predefined consistency criterion, whereas it accepts EP parameters that satisfy the consistency criterion. The processor updates the 3D map by superimposing onto the map an overlay, indicating the values of the accepted sets of EP parameters. The indication may be, for example, a color code, wherein the lowest value of the EP parameter is denoted by blue, the highest by red, and the intermediate values by the colors of the visible spectrum between blue and red. When several sets of EP parameters are accepted in a given area, the processor may overlay the 3D map with, for example, an average of the accepted sets. Alternatively, the processor may overlay the accepted sets onto the map one after the other, or overlay it with only one of the accepted sets.

System Description

Figure 1:
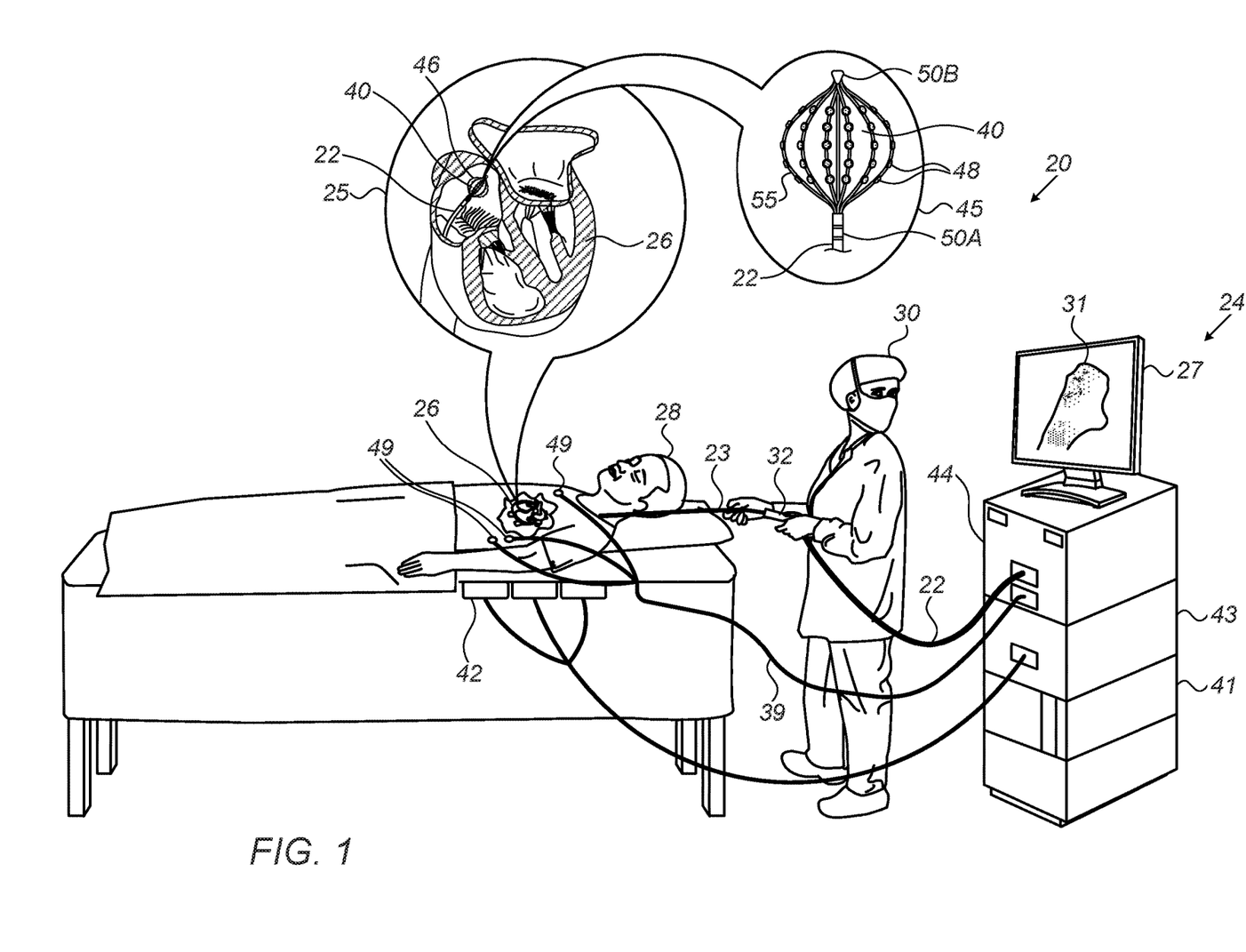
FIG. 1 is a schematic pictorial illustration of a medical apparatus for mapping an EP parameter in a heart of a patient, in accordance with an embodiment of the present invention.

FIG. 1 is a schematic pictorial illustration of a medical apparatus 20 for mapping an EP parameter in a heart 26 of a patient 28, in accordance with an embodiment of the present invention.

A physician 30 navigates a basket catheter 40, seen in detail in an inset 45, to a target location in heart 26 of patient 28, by manipulating a shaft 22, using a manipulator 32 near the proximal end of the catheter, and/or deflection from a sheath 23. In the embodiment seen in an inset 25, physician 30 uses catheter 40 to perform electro-anatomical mapping of a cardiac chamber. EP signals are acquired from tissue by using a group of electrodes 48 on basket catheter 40 touching the tissue in an area 46, as further detailed below. When a basket catheter is used, the group of electrodes is in general a smaller subset of the total number of electrodes 48, for example, 20 out of a total of 120 electrodes.

Catheter 40 is inserted in a collapsed configuration, through sheath 23, and only after the catheter exits sheath 23 does the catheter expand to its intended functional shape, as shown in inset 45. By containing catheter 40 in a collapsed configuration, sheath 23 also serves to minimize vascular trauma on its way to the target location.

Basket catheter 40 incorporates a magnetic sensor 50A, seen in inset 45, at the distal edge of shaft 22 (i.e., at the proximal edge of basket catheter 40). Typically, although not necessarily, sensor 50A is a Triple-Axis Sensor (TAS), comprising three miniature coils oriented in different directions. In the pictured embodiment, a second magnetic sensor 50B is incorporated in a distal edge of the basket catheter. Sensor 50B may be a Single-Axis Sensor (SAS) or a Triple-Axis Sensor (TAS), for example. Alternatively, catheter 40 may comprise other sorts of magnetic sensors, at these or other locations.

Catheter 40 further comprises multiple expandable spines 55, which may be mechanically flexible, to each of which are coupled multiple electrodes 48 for a total of, for example, 120 electrodes. Electrodes 48 are configured to touch the tissue of patient 28 for sensing EP signals. Magnetic sensors 50A and 50B and electrodes 48 are connected by wires running through shaft 22 to various processing circuits in a console 24.

Alternatively, apparatus 20 may comprise other types of catheters, with other sorts of electrode arrays, such as an inflatable balloon catheter with electrodes 48 on its outer surface.

Medical apparatus 20 comprises a magnetic-sensing subsystem for determining the position and orientation of basket catheter 40, and thereby the positions of electrodes 48. Patient 28 is placed in a magnetic field generated by a pad containing magnetic field generator coils 42, which are driven by a tracking module 43 in console 24. The magnetic fields generated by coils 42 give rise to electrical signals in sensors 50A and 50B, which are indicative of the position and/or orientation of the sensors. The signals form sensors 50A and 50B are transmitted back to tracking module 43, which converts the signals to corresponding digital inputs to a processor 41. Processor 41 uses these inputs to calculate the position and orientation of basket catheter 40 and thus to find the respective location of each of electrodes 48.

Methods of position and/or orientation sensing using external magnetic fields and magnetic sensors, such as sensors 50A and 50B, are implemented in various medical applications, for example, in the CARTO® system, available from Biosense Webster, Inc. (Irvine, Calif.). Such methods are described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference with a copy provided in the Appendix.

Alternatively or additionally, apparatus 20 may use other methods of position sensing to find the locations of electrodes 48. For example, processor 41 may map the locations of electrodes 48 by measuring impedances between electrodes 48 and body-surface electrodes 49, which are placed on the chest of patient 28 and connected to console 24 by leads 39.

Processor 41 additionally receives electrophysiological signals via electrical interface 44, and uses the information contained in these signals together with the coordinates provided by magnetic sensors 50A and 50B to construct an electro-anatomical map 31 of the chamber of heart 26 in which catheter 40 is located. During and/or following the procedure, processor 41 may render electro-anatomical map 31 to a display screen 27 (detailed further in FIG. 3.)

Processor 41 is typically programmed in software to carry out the functions described herein. The software may be downloaded to the computer in electronic form, over a network, for example, or it may, alternatively or additionally, be provided and/or stored on non-transitory tangible media, such as magnetic, optical, or electronic memory. In particular, processor 41 runs a dedicated algorithm that enables the processor to perform the disclosed steps, as described below.

The example illustration shown in FIG. 1 is chosen purely for the sake of conceptual clarity. FIG. 1 shows only elements related to the disclosed techniques for the sake of simplicity and clarity. Medical apparatus 20 typically comprises additional modules and elements that are not directly related to the disclosed techniques, and thus are intentionally omitted from FIG. 1 and from the corresponding description. The elements of medical apparatus 20 and the methods described herein may be further applied, for example, to control an ablation of tissue of heart 26.

Measurement and Display of EP Parameters

Figure 2:
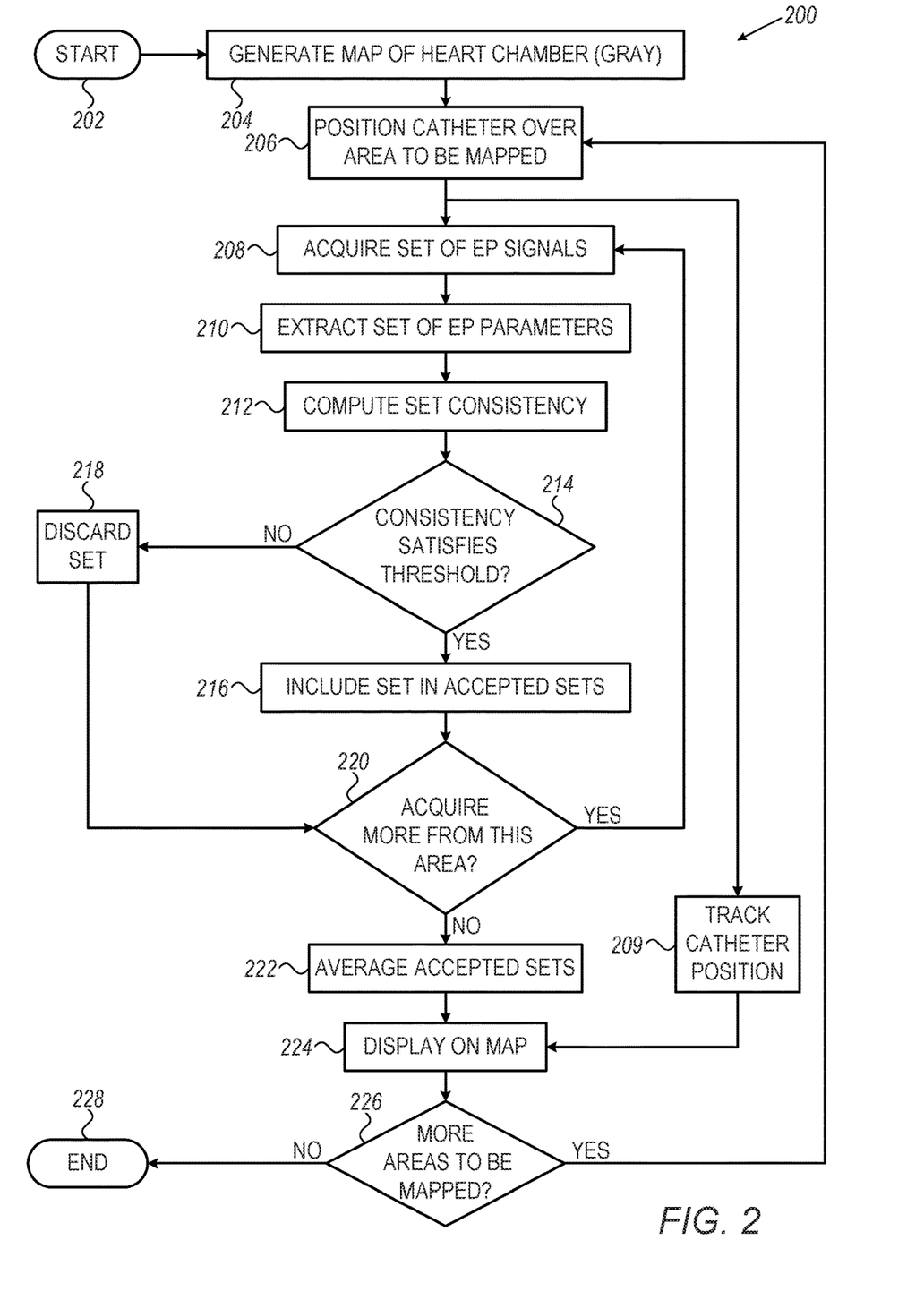
FIG. 2 is a flowchart that schematically illustrates a method for automated EP mapping, in accordance with an embodiment of the invention.

FIG. 2 is a flowchart 200 that schematically illustrates an automated process for EP mapping, in accordance with an embodiment of the invention. In this method, EP parameters from area 46 are incorporated in the map only when they satisfy a certain consistency criterion. The embodiment shown in flowchart 200 refers to an example of acquiring EP signals from a chamber of heart 26 (with reference to FIG. 1). In alternative embodiments, the values of EP parameters may be acquired using other sorts of mapping apparatus, not only from the heart, but also from other organs and tissue, as will be apparent to those skilled in the art after reading the present description.

The process illustrated by flowchart 200 begins in a start step 202. In a map generation step 204, a uniformly gray (or other suitable background color) 3D map of the heart chamber is generated by processor 41 and rendered onto display screen 27. The 3D map is generated, for example, from an image of heart 26 previously stored in the processor, or based on position measurements taken by a catheter. Alternatively, the 3D map may be generated concurrently with displaying the EP parameters. In a catheter positioning step 206, physician 30 positions catheter 40 in heart 26 so that a group of electrodes 48 are in contact with myocardial tissue in area 46 of a chamber of the heart. In an acquisition step 208, processor 41 receives, during a single time interval (such as a single heartbeat) signals from the group of electrodes 48. In a tracking step 209, processor 41 receives signals from tracking module 43, and computes the respective location coordinates of electrodes 48. In an extraction step 210, processor 41 extracts the set of EP parameters from the signals received in acquisition step 208.

In a consistency computation step 212, processor 41 computes the measure of consistency for the set of EP parameters extracted in extraction step 210. The measure of consistency, as well as the consistency criterion, are defined in the present embodiment in terms of the peak-to-peak variation of the EP parameters across a given set. For example, when the EP parameter computed in step 210 is the local activation time (LAT), the consistency criterion can be taken as a range of ±10 ms, i.e., if the LATs within the set are within 20 ms of each other, they are considered to satisfy the consistency criterion. In another example, when the EP parameter is a bipolar or unipolar maximum voltage in the signals sensed by electrodes 48, the consistency criterion can be taken as a range of 20 mV, so that measured maximum voltages within this range are considered to satisfy the consistency criterion. Alternatively, larger or smaller ranges of the parameters can be taken as the consistency criterion.

Further alternatively, other sorts of consistency criteria can be applied. For example, processor 41 may compute the mean value of the EP parameter in question and the variance of the parameter over the sequence of heartbeats, and may define the consistency criterion in terms of the maximal acceptable variance.

In a first decision step 214, processor 41 compares the measure of consistency computed in step 212 to the pre-defined consistency criterion. If the measure of consistency satisfies the consistency criterion, processor 41 includes the set of EP parameters in the accepted sets, in an inclusion step 216. If the measure of consistency does not satisfy the criterion, processor 41 discards the set of EP parameters, in a discard step 218.

Both from inclusion step 216 and discard step 218, the process continues to a second decision step 220, where processor 41 determines, based on a preset criterion, whether more sets of EP parameters are to be acquired from the current area 46. Additional acquisitions may be required, if, for example, the measure of consistency did not satisfy the consistency criterion for any of the sets of EP parameters acquired from the current area 46. Alternatively or additionally, further acquisitions may be desirable in order to average over a large number of accepted sets. When more acquisitions are required, the process returns to step 208.

When no more acquisitions are required, the sets of EP parameters collected in step 216 may optionally be averaged in an averaging step 222. Alternatively, averaging step 222 may be bypassed, and only one of the accepted sets of EP parameters may be chosen for output. A representation of the resulting EP parameters (averaged or not) is superimposed on the 3D map in a display step 224. In a display step 224, processor 41 displays the EP parameters, for example by applying a corresponding color code to the appropriate region of the 3D map generated in step 204, based on the position coordinates received in tracking step 209. The color-coding may comprise, for example, showing the lowest values of the EP parameter as a blue color, the highest values as a red color, and intermediate values between the lowest and highest values in the same order as colors in a visible spectrum. However, other color-coding schemes, as well as other sorts of shading or symbols, such as are known in the art, may alternatively be used.

After display step 224, the process continues to a third decision step 226, where physician 30 decides whether additional areas will be included in the mapping. When the decision is affirmative, physician 30 moves catheter 40 into a new area 46 in step 206, and the process continues from there as described above. When physician 30 decides that the mapping has been completed, the process ends in an end step 228.

Figure 3:
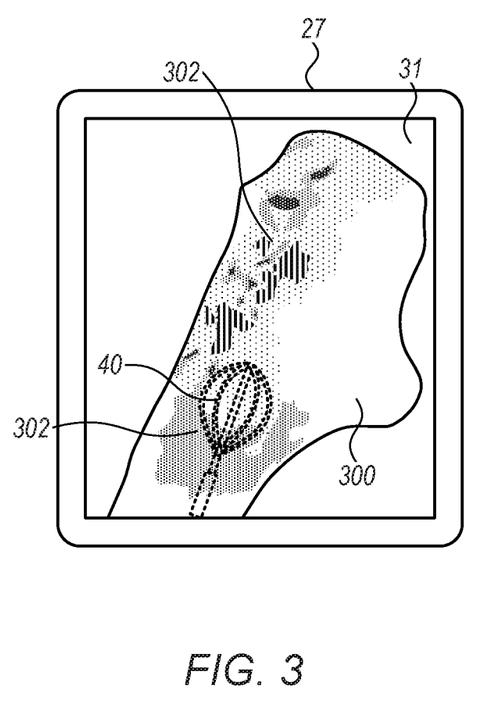
FIG. 3 is a schematic illustration of an electro-anatomical map, in accordance with an embodiment of the invention.

FIG. 3 is a schematic illustration of electro-anatomical map 31, in accordance with an embodiment of the invention. A 3D map 300 is initially colored in a neutral color, such as gray, on display screen 27, following step 204 (FIG. 2). When the EP parameters acquired by basket catheter 40 satisfy the applicable consistency criterion, a colored overlay 302 is superimposed on 3D map 300 in accordance with the method of FIG. 2.

Although the embodiment described above relates to measurement of EP parameters in heart 26, in alternative embodiments the described method of automated acceptance or rejection of EP parameters may be applied to other tissues of the body of patient 28. Moreover, in alternative embodiments more than one type of EP parameter may be measured and displayed simultaneously.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:
1. A medical system comprising:
a processor; and
a memory in communication with the processor and storing instructions configured to cause the medical system to:
receive a plurality electrophysiological signals during a first time interval from a plurality of electrodes, the plurality of electrodes being coupled to a catheter and in contact with tissue;
extract electrophysiological parameters from the plurality of electrophysiological signals;
determine a measure of consistency of the electrophysiological parameters, the measure of consistency comprising a variation range of the electrophysiological parameters;
determine whether the variation range is in a predetermined variation range;
determine whether additional electrophysiological parameters are required;
in response to determining that additional electrophysiological parameters are required, receive a plurality of additional electrophysiological signals from the plurality of electrodes during a second time interval;
extract additional electrophysiological parameters from the plurality of additional electrophysiological signals;
determine an additional measure of consistency among the additional electrophysiological parameters, the additional measure of consistency comprising an additional variation range of the additional electrophysiological parameters;
determine whether the additional variation range is in the predetermined variation range;
in response to determining that the additional variation range is in the predetermined variation range, determine an average value of the electrophysiological parameters and the additional electrophysiological parameters; and
output a representation of the average value to a display.

2. The medical system of claim 1 further comprising:
in response to determining that the variation range is outside the predetermined variation range, discard the electrophysiological parameters.

3. The medical system of claim 1, the electrophysiological parameters comprising local activation times of myocardial tissue.

4. The medical system of claim 3, the predetermined variation range comprising a span of 20 milliseconds between a maximum value and a minimum value.

5. The medical system of claim 1, the electrophysiological parameters comprising an electrophysiological voltage of the plurality of electrophysiological signals.

6. The medical system of claim 5, the predetermined variation range comprising about 20 millivolts.

7. The medical system of claim 1, the plurality of electrophysiological signals being received from myocardial tissue;
the first time interval spanning a plurality of heartbeats; and
the instructions are further configured to cause the medical system to determine a mean value of the electrophysiological parameters over the plurality of heartbeats.

8. The medical system of claim 7, wherein determining the measure of consistency of the electrophysiological parameters is based on the mean value of the electrophysiological parameters.

9. The medical system of claim 1 the instructions being further configured to cause the medical system to receive position data indicative of a position of the catheter; and
wherein outputting the representation of the electrophysiological parameters to the display comprises rendering to the display a three-dimensional map of the tissue while superimposing on the map a visual indication of the electrophysiological parameters based at least in part on the position data.

10. The medical system of claim 9, the position data being received from a position-tracking system configured to acquire position coordinates of the catheter.

11. The medical system of claim 1, the catheter comprising a basket catheter.

12. The medical system of claim 1, the electrophysiological parameters comprising at least two different types of electrophysiological parameters.

13. A method of mapping electrophysiological parameters, the method comprising:
receiving a first plurality of electrophysiological signals during a first time interval from a plurality of electrodes, the plurality of electrodes being coupled to a catheter and in contact with tissue;
extracting first electrophysiological parameters from the first plurality of electrophysiological signals;
determining whether additional electrophysiological parameters are required;
in response to determining that additional electrophysiological parameters are required, receiving a second plurality electrophysiological signals during a second time interval from the plurality of electrodes;
extracting a second plurality of electrophysiological parameters from the second plurality of electrophysiological signals;
determining a first measure of consistency of the first electrophysiological parameters and comparing the first measure of consistency to a threshold measure of consistency;
determining a second measure of consistency of the second electrophysiological parameters and comparing the second measure of consistency to the threshold measure of consistency;
in response to determining that the first measure of consistency and the second measure of consistency each satisfy the threshold measure of consistency, determining an average value of the first electrophysiological parameters and the second electrophysiological parameters; and
outputting a representation of the average value to a display.

14. The method of claim 13 further comprising:
receiving position data indicative of a position of the catheter; and
wherein outputting a representation of the electrophysiological parameters to the display is based at least in part on the position data.

15. The method of claim 14, wherein outputting the representation of the average value to the display comprises rendering to the display a three-dimensional map of the tissue while superimposing on the map a visual indication of the average value based at least in part on the position data.

16. The method of claim 13, the first measure of consistency comprising a first variation range of the first electrophysiological parameters, and
the second measure of consistency comprising a second variation range of the second electrophysiological parameters.

17. The method of claim 13 further comprising:
in response to determining that the first measure of consistency or the second measure of consistency is outside the threshold measure of consistency, discard the first electrophysiological parameters or the second electrophysiological parameters respectively.

18. The method of claim 13, the first electrophysiological parameters and the second electrophysiological parameters each comprising local activation times of myocardial tissue.

19. The method of claim 13, the first electrophysiological parameters and the second electrophysiological parameters each comprising an electrophysiological voltage of the first plurality of electrophysiological signals and the second plurality of electrophysiological signals.

* * * * *